US00PP08494P

United States Patent [19]

Tracy

[11] Patent Number: Plant 8,494

[45] Date of Patent: Dec. 14, 1993

[54] HYBRID TEA ROSE PLANT NAMED 'HILAROMA'

[75] Inventor: Daniel Tracy, Richmond, Ind.

[73] Assignee: The Conard-Pyle Company, West Grove, Pa.

[21] Appl. No.: 958,731

[22] Filed: Oct. 9, 1992

[51] Int. Cl.[5] ..... A01H 5/00

[52] U.S. Cl. ..... Plt./11

[58] Field of Search ..... Plt./11, 12, 13, 22

[56] References Cited

U.S. PATENT DOCUMENTS

P.P. 5,067 7/1983 Meilland ..... Plt. 11

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive bicolored blossoms. The blossoms are Naples Yellow and strongly edged with Venetian Pink on opening and turning to Neyron Rose when fully open. The blossoms exhibit a strong spicy fragrance. Such blossoms are long lasting and their cleaning ability is excellent. The plant exhibits a bushy growth habit, very vigorous vegetation, very leathery foliage, and is particularly well suited for growing in parks and gardens. Also, the new variety is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Pristine variety (U.S. Plant Pat. No. 3,997), and the male parent (i.e., the pollen parent) was the Friendship variety (U.S. Plant Pat. No. 4,284). The parentage of the new variety can be summarized as follows:

Pristine × Friendship.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive very fragrant long lasting bicolored fully double flowers which are Naples Yellow and strongly edged with Venetian Pink on opening and turning to Neyron Rose when fully open,
(b) exhibits a bushy growth habit,
(c) exhibits very vigorous vegetation,
(d) forms foliage which is very leathery, and
(e) is not particularly affected by cryptogamic diseases.

The strong spicy fragrance of the blossoms is particularly noteworthy. The disease resistance of the new variety is above average.

The new variety well meets the needs of the horticultural industry for a number of uses and is particularly well suited for growing as attractive ornamentation in parks and gardens.

The new variety has been found to undergo asexual propagation at Richmond, Ind., and West Grove, Pa.

U.S.A. by a number of routes, including budding, grafting, cuttage, etc. The characteristics of the new variety have been found to be strictly transmissible by such asexual propagation from one generation to another.

The new variety has been named the Hilaroma variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were three years of age and were observed during September while budded on *Rosa froebelii* understock and growing outdoors at West Grove, Pa., U.S.A.

From left to right on the top row are shown a specimen of a young shoot, a specimen of a leaf with three leaflets—plan view—upper surface, a specimen of a floral bud before the opening of the sepals, a specimen of a floral bud at the opening of the sepals, a specimen of a floral bud at the opening of the petals, and a specimen of a flower during the course of opening.

From left to right on the second row are shown a specimen of a leaf with five leaflets—plan view—under surface, a specimen of a leaf with five leaflets—plan view—upper surface, a specimen of an opening flower—plan view—obverse, a specimen of an opening flower—plan view—reverse, at the top a specimen of a floral receptacle showing the arrangement of the stamens and pistils, and at the bottom a specimen of a floral receptacle showing the arrangement of the pistils (stamens removed).

From left to right on the third row are shown a specimen of a leaf with seven leaflets—plan view—under surface, a specimen an open flower—plan view—obverse, and a specimen of an open flower—plan view—reverse.

From left to right on the bottom row are shown a specimen of a main stem, a specimen of a flowering stem, a specimen of a fully open flower—plan view—reverse, and a specimen of a fully open flower—plan view—obverse.

DETAILED DESCRIPTION

The chart used in the identification of the colors is that of the Royal Horticultural Society (R.H.S. Colour Chart). The description is based on the observation of three year old plants made during September while budded on *Rosa froebelii* understock and growing outdoors at West Grove, Pa., U.S.A. The coloration in common terms sometimes is presented.

Class: Hybrid Tea.

Plant:

*Height.*—At the end of two growing seasons the height is approximately 1.4 to 1.5 m. and the width is approximately 1.4 m.

*Habit.*—Bushy.

Branches:

*Color.*—Young stems: Greyed-Orange Group 166A, and strongly stained with greenish coloration. Adult wood: Yellow-Green Group 146B.

*Thorns.*—Size: medium. Quantity: very few and almost nonexistent on young wood. Color: reddish-green on young stems and reddish with greenish tips on adult wood.

Leaves:

*Stipules.*—Adnate, pectinate, somewhat wide and linear.

*Petioles.*—Length: approximately 3 cm. on average. Upper surface: reddish brown on young foliage and reddish-green on adult foliage. Under surface: reddish-brown on young foliage, medium green on adult foliage, and reddish prickles rarely are present.

*Leaflets.*—Number: 3, 5 (most often), and 7. Shape: oval. Serration: single and regular. Texture: leathery. General Appearance: dense, dark matte foliage. Color (young foliage): Upper surface: Greyed-Purple Group 187A. Under surface: Greyed-Purple Group 183D. Color (adult foliage): Upper surface: Yellow-Green Group 147A. Under surface: Yellow-Green Group 147B.

Inflorescence:

*Number of flowers.*—Normally 1 to 5 per stem, and most often 1 to 3 per stem.

*Peduncle.*—Smooth, straight, reddish-green in coloration, and bears very few prickles. The length is approximately 6.5 to 7.5 cm. on average.

*Sepals.*—Upper surface: tomentose, and greenish stained with reddish coloration towards the middle. Under surface: light green and widely stained with reddish coloration, and the outer sepals often bear leaf-like appendices on the edges.

*Buds.*—Shape: ovoid. Length: approximately 4 cm. on average before opening. Size: large. Color upon opening: Upper surface: Yellow Group 11B, suffused and edged with reddish coloration. Under surface: Yellow Group 11B.

*Flower.*—Shape: cup-like and fully double. Diameter: approximately 12 cm. on average when fully open. Color (when opening begins): Upper surface: Yellow Group 11D at the center of the petal, changing to Red Group 49D, and edged and suffused with Red Group 55B. Under surface: Yellow Group 11C, suffused with Red Group 49B, and edged with Red Group 50A on the outer petals. Color outer petals (when blooming): Upper surface: Red Group 49A, strongly suffused with Red Group 48C, and Red Group 50B towards the outside of the petal. Under surface: Red Group 49C, and strongly suffused with Red Group 50C, and having a wide yellowish-white claw. Color inner petal (when blooming): Upper surface: Yellow Group 11D, and edged with Red Group 49B. Under surface: Yellow Group 11C, edged with Red Group 49B, and blending progressively to Yellow Group 11B and Yellow Group 11A towards the point of attachment. Color outer petals (at end of blooming): Upper surface: Red Group 49C towards the center and changing progressively to Red Group 49B, light Red Group 49B, and light Red Group 49A towards the edge of the petal. Under surface: Red Group 49D, and stained with Red Group 55B. Color inner petals (at end of blooming: Upper surface: Yellow Group 11A near the point of attachment, turning to Red Group 49D at the center of the petal, and edged with Red Group 55B. Under surface: Yellow Group 11C near the point of attachment, turning to Red Group 49D at the center of the petal, and edged with Red Group 55B. Fragrance: very strong spicy. Lasting quality: long when cut or left on the plant. Petal number: approximately 28 to 30 on average plus a few petaloids. Texture: consistent. Petal drop: very good. Petal configuration: rounded. Stamen number: approximately 110 to 125 on average. Anthers: normal, strawlike. Filaments: normal, reddish at the base and turning yellow near the anthers, and of irregular heights. Pistils: approximately 95 to 110 on average, and located above the stamens. Stigmas: normal, whitish. Styles: very twisted, tomentose, whitish turning reddish near the top, and of irregular heights. Receptacle: smooth, light green, and in longitudinal section at the dehiscence of the anthers it is in the shape of a funnel.

Development:

*Vegetation.*—Very vigorous and bushy.

*Blooming.*—Abundant and continuous.

*Aptitude to bear fruits.*—Poor.

*Resistance to frost.*—Good.

*Resistance to diseases.*—Good.

I claim:

1. A new and distinct variety of the Hybrid Tea rose plant characterized by the following combination of characteristics:

(a) forms in abundance on a continuous basis attractive very fragrant long lasting bicolored fully double flowers which are Naples Yellow and strongly edged with Venetian Pink on opening and turning to Neyron Rose when fully open, (b) exhibits bushy growth habit, (c) exhibits very vigorous vegetation, (d) forms foliage which is very leathery, and (e) is not particularly affected by cryptogamic diseases;

substantially as herein shown and described.

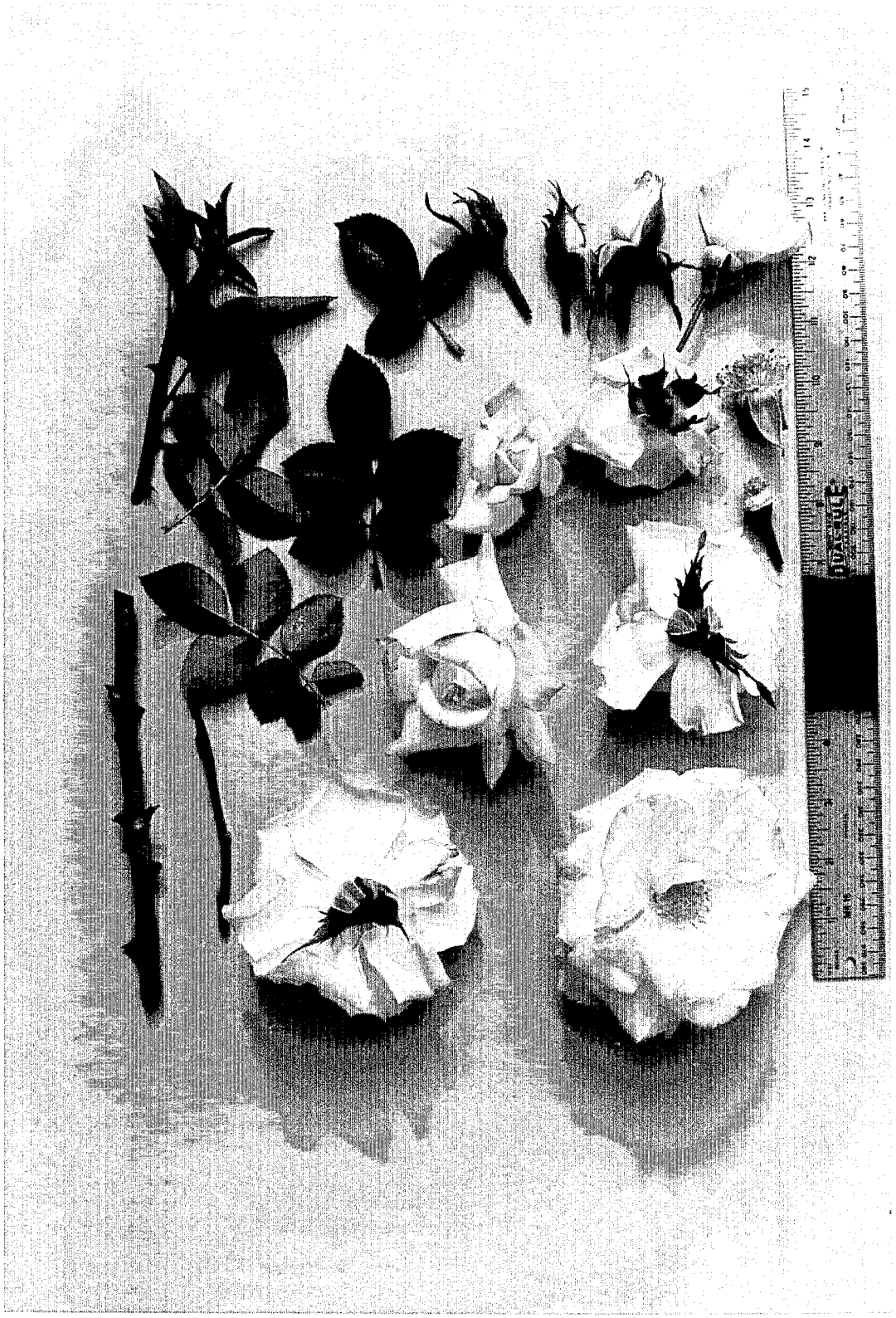

* * * * *